(12) United States Patent  
Payne et al.

(10) Patent No.: US 6,620,107 B2
(45) Date of Patent: Sep. 16, 2003

(54) DETECTION OF CONDITIONS BY ANALYSIS OF GASES OR VAPOURS

(75) Inventors: Peter Alfred Payne, Knutsford (GB); Krishna Chandra Persaud, Cheadle (GB); Allan John Syms, Lach Dennis (GB)

(73) Assignee: Osmetech plc (GB)

( * ) Notice: Subject to any disclaimer, the term of this patent is extended or adjusted under 35 U.S.C. 154(b) by 0 days.

(21) Appl. No.: 10/025,544

(22) Filed: Dec. 18, 2001

(65) Prior Publication Data

US 2002/0151814 A1 Oct. 17, 2002

Related U.S. Application Data

(63) Continuation of application No. 09/380,541, filed as application No. PCT/GB98/00510 on Mar. 6, 1998, and a continuation-in-part of application No. PCT/GB97/03543, filed on Dec. 24, 1997.

(30) Foreign Application Priority Data

Mar. 6, 1997 (GB) ................................. 9704676

(51) Int. Cl.[7] ................................................ A61B 5/00
(52) U.S. Cl. ............................ 600/532; 73/23.3; 422/84
(58) Field of Search .......................... 600/532; 73/23.3; 422/84

(56) References Cited

U.S. PATENT DOCUMENTS

| 4,314,564 A | 2/1982 | Albarda | |
|---|---|---|---|
| 4,671,298 A | 6/1987 | Babb et al. | |
| 4,772,559 A | 9/1988 | Preti et al. | 600/532 |
| 5,361,771 A | 11/1994 | Craine et al. | 600/532 |
| 5,425,374 A | 6/1995 | Ueda et al. | 600/532 |
| 5,787,885 A | 8/1998 | Lemelson | 600/532 |
| 5,789,660 A | 8/1998 | Kofoed et al. | 600/532 |
| 5,848,975 A | 12/1998 | Phillips | 600/532 |
| 6,067,989 A | 5/2000 | Katzman | 600/532 |
| 6,319,724 B1 * | 11/2001 | Lewis et al. | 422/84 |
| 6,461,306 B1 * | 10/2002 | Hanson, III et al. | 600/532 |
| 6,465,728 B1 | 10/2002 | McLaughlin et al. | 600/532 |
| 6,467,333 B2 * | 10/2002 | Lewis et al. | 73/23.01 |

FOREIGN PATENT DOCUMENTS

| EP | 0 158 497 | 10/1985 |
|---|---|---|
| WO | WO 94/04705 | 3/1994 |
| WO | WO 95/33848 | 12/1995 |

OTHER PUBLICATIONS

"No business like nose business," *The Independent* (Feb. 14, 1994), 2 pp.
Gardner and Craven; "Classification of Bacteria Age and Type Using and Array of Metal Oxide Sensors & Pattern Recognition Techniques"; 3rd International Symposium on Olfaction and Electronic Noses; Nov. 3–6, 1996.
Rosenberg(Ed); "Bad Breath: Research Perspectives" 1995.
Rossi et al. "Rapid Discrimination of Meat Products and Bacterial Strains Using Semiconductor Gas Sensors"; Bioflavour 95 Feb.14–17; pp. 85–89.
Parry et al.; "Detection of B–haemolytic Streptococcal Infection by Analysis of Leg Ulcer Odour"; Annual Conference of Wound Management; Oct. 1994; pp. 134–137.
Craven et al.; "Application of an Artificial Neural Network Based Electronic Nose to the Classification of Bacteria"; EUFIT, 1994; pp. 768–774.

(List continued on next page.)

*Primary Examiner*—Robert L. Nasser
(74) *Attorney, Agent, or Firm*—Marger Johnson & McCollom, PC

(57) ABSTRACT

A method for detecting the occurrence of a condition in a respiring subject includes the steps of: introducing emitted subject respiratory gases to a gas sensing device; detecting certain species present in the emitted subject respiratory gases with the gas sensing device; and correlating the presence of the species with the occurrence of the condition.

19 Claims, 2 Drawing Sheets

OTHER PUBLICATIONS

Schweizer–Berberich et al.; "Characterisation of Food Freshness with Sensor Arrays"; Sensors and Actuators B 18–19; (1994); pp. 282–290.

Berdague et al.; "Revue Caracterisation Instrumentale de la Qualite des Matieres Premieres et des Aliments par Analyse des Composes Volatils"; Viandes Prod. Carnes 14(5) 1993 135 Sep.–Oct.; pp. 135–138.

Winquist et al.; "Performance of an Electronic Nose for Quality Estimation of Ground Meat"; Meas. Sci. Technol. 4(1993) 1493–1500.

Cowan and Steel's Manual for the Identification of Medical Bacteria; $3^{rd}$ Edition 1993.

MIDI Technical Notes #101; "Identification of Bacteria by Gas Chromatography of Cellular Fatty Acids"; May 1990; pp. 163–169.

MIDI Technical Notes #102; "Tracking a Strain Using the Microbial Identification System'"; May 1990; pp. 171–174.

Ray Clement (Ed); "Gas Chromatography Biochemical, Biomedical and Clinical Applications"; 1990; pp. 327–347.

Shen–Wu Ho; Chinese J. Microbio Immunol. 19, (1986); "Head Space Gas Liquid Chromatographic Analysis for Presumptive Identification of Bateria on Blood Cultures"; pp. 18–26.

Shiyousou, Patent Abstracts of Japan JP 60130398 (Nov. 7, 1985).

Schneider et al. Digestion 32: 86–91 (1985); "Value of the $^{14}$C–D–Xylose Breath Test in Patients with Intestinal Bacterial Overgrowth"; pp. 86–91.

Persaud, K.C. and P. Pelosi. "Sensor Arrays Using Conducting Polymers for an Artificial Nose." *Sensors and sensory Systems for an Electronic Nose.* pp. 237–256. eds. J.W. Gardner and P.N. Bartlett, 1992.

J.W. Gardner and Phillip N. Barlett, "A brief history of electronic noses", *Sensors and Actuators B,* 18–19 (1994), pp. 211–220.

"Aroma Scan sniffs our medical applications", *Clinica* (May, 1994), pp. 20–21.

Patent Abstracts of Japan; vol. 96, No. 4, Apr. 30, 1996 & JP 07 323034 A (Hitachi Ltd), Dec. 12, 1995.

International Search Report; PCT/GB98/00501; Apr. 22, 1998; C. Van Bohemen.

* cited by examiner

DETECTION OF CONDITIONS BY ANALYSIS OF GASES OR VAPOURS

This application is a continuation (and claims the benefit of priority under 35 USC 120) of U.S. application Ser. No. 09/380,541, filed on Oct. 7, 1999; which is a 371 of PCT/GB 98/00510, filed on Mar. 6, 1998; and a continuation-in-part of PCT/GB 97/03543, filed on Dec. 24, 1997. The disclosure of the prior application is considered part of (and is incorporated by reference in) the disclosure of this application.

It is known that the breath odour can provide an indication of certain conditions. A straightforward example is that of halitosis, or "bad breath". Another example is ketosis, wherein the presence of sweet smelling ketones and aldehydes in the breath can be an indication of diabetes.

The present invention provides a method and apparatus for detection numerous conditions from the gaseous or volatile species present in breath. For the avoidance of doubt, the terms "gas" and "gases" are taken to comprise any species present in the gas phase, including vapours from volatile liquids.

According to a first aspect of the invention there is provided a method for detecting the occurrence of a condition in a respiring subject comprising the steps of:

introducing emitted subject repiratory gases to a gas sensing device;

detecting certain species present in said emitted subject respiratory gases with said gas sensing device; and correlating the presence of said species with the occurrence of the condition.

The method is rapid, since the analysis is direct—there is no need to perform time consuming culturing steps. Furthermore, the method provides non-invasive clinical screening and monitoring of many conditions.

The respiring subject may be human.

The gas sensing device may comprise an array of semiconducting organic polymer gas sensors.

The gas sensing device may comprise a gas sensitive material, of which an electrical property may vary on exposure to gases. The gas sensitive material may comprise semiconducting organic polymer.

The gas sensing device may comprise a mass spectrometer or a GC-MS device.

The emitted respiratory gases may be obtained from a ventilator. In this way, on-line monitoring for the occurrence of a condition, or monitoring of the progress of a condition, is possible.

The emitted subject respiratory gases may be introduced directly to the gas sensing device.

The occurrence of an infection or a disease state may be detected.

The occurrence of a lung disorder may be detected, which may be pneumonia, tuberculosis or a yeast infection.

The occurrence of a gastrointestinal infection may be detected.

The occurrence of diabetes may be detected.

The presence of alcohol may be detected.

The occurrence of phenylketonuria may be detected.

According to a second aspect of the invention there is provided a detector for detecting the occurrence of a condition in a respiring subject comprising a gas sensing device and means for introducing emitted subject respiratory gases to the gas sensing device, which device is adpated to recognise the occurrence of a condition in the subject when certain species present in said emitted respiratory gases are detected.

The means for introducing emitted respiratory gases to the gas sensing device may comprise a ventilator. The gas sensing device may be directly connected to the ventilator.

Methods and apparatus in accordance with the invention will now be described with reference to the accompanying drawings, in which.

Figure 1:
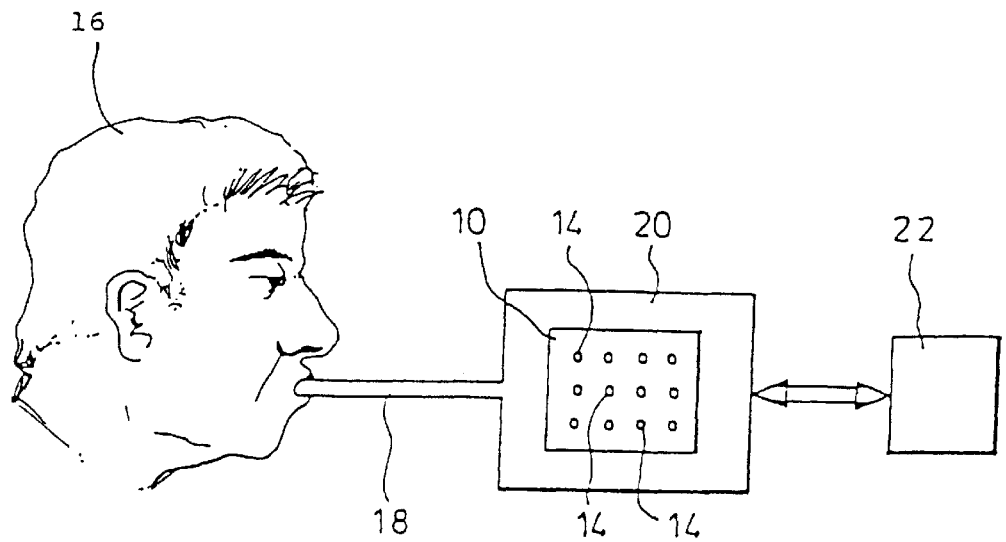
FIG. 1 shows a first detector according to the invention.

The invention comprises a method for detecting the occurrence of a condition in a respiring subject comprising the steps of:

introducing emitted subject respiratory gases to a gas sensing device;

detecting certain species present in said emitted subject respiratory gases with said gas sensing device; and correlating the presence of said species with the occurrence of the condition.

The method is primarily directed towards humans, although it will be apparent that it lends itself to the detection of conditions in many animals.

The gas sensing device 10 comprises an array 12 of semiconducting organic polymer gas sensors 14, the presence of gases being detected by monitoring variations in the dc resistances of said sensors 14. Such devices are manufactured, for example, by AromaScan plc, Crewe, UK. There are many semiconducting organic polymers suitable for such devices: examples include polypyrrole and polyindole and substituted variants thereof. It is a property of such polymer that the adsorption of certain (usually polar) gases causes measurable conductivity changes, and hence such gases may be detected by monitoring changes in the dc resistance of the polymer. Because each polymer typically exhibits quite broad band sensitivities, an array of gas sensors are employed. This permits selective identification of a wide range of gases by recognising the characteristic "fingerprint" of response across the array (see, for example, J V Hatfield, P Neaves, P J Hicks, K Persaud and P Travers, Sensors & Actuators B, 18–19 (1994) 221–228). The output of the sensors 14 is analysed by analysis means 22, which correlates the output pattern of sensor response with the occurrence of certain conditions. The analysis means 22 is usually a computer or microprocessor. A single such device can be used to recognise a number of conditions. The use of a trained neural network is particularly advantageous in this regard.

It is also possible to interrogate semiconducting organic polymers by applying ac electrical signal thereto and monitoring an impedance quantity of the polymers, or variations in such an impedance quantity, as a function of the frequency of the applied ac electrical signal (see, for example, British Patent GB 2 203 553 and M E H Amrani, R M Dowdeswell, P A Payne and K C Persaud, Proceedings of Eurosensors X, Vol. 2, (1996) pp 665–668). Using this approach, a single semiconducting organic polymer sensor can provide information equivalent, or actually superior, to that provided by an array of such sensors interrogated by the dc resistance technique.

Other types of gas sensors which comprise a gas sensitive material might be employed, such as metal oxide semiconductor (MOS), quartz resonator or surface acoustic wave (SAW) devices. An array comprising a plurality of such devices would be utilised. Alternatively, a mass spectrometry or a GC-MS device might be used. Alternatively still, spectroscopic techniques such as infra-red spectroscopy might be employed.

Advantageously, the emitted subject respiratory gases are introduced directly to said gas sensing device 10. As shown in FIG. 1, this might be accomplished by a subject 16 exhaling into a tube 18, the tube 18 being in communication with a region 20 containing the gas sensing device 10. The gas sensing device 10 might be purged with a inert gas, such as nitrogen, and a one-way valve might be positioned between the tube 18 and the gas sensing device 10, in order to retain the atmosphere of inert gas until the subject 16 exhales. Alternatively, the subject 16 may exhale into a receptacle, such as a bag, which is sealable so as to retain a headspace which may subsequently be introduced to the gas sensing device 10. The entire detector, comprising the gas sensing device 10 and the means 18 for introducing respiratory gases to the gas sensing device 10, might be provided as a portable, possibly hand-held device.

Figure 2:
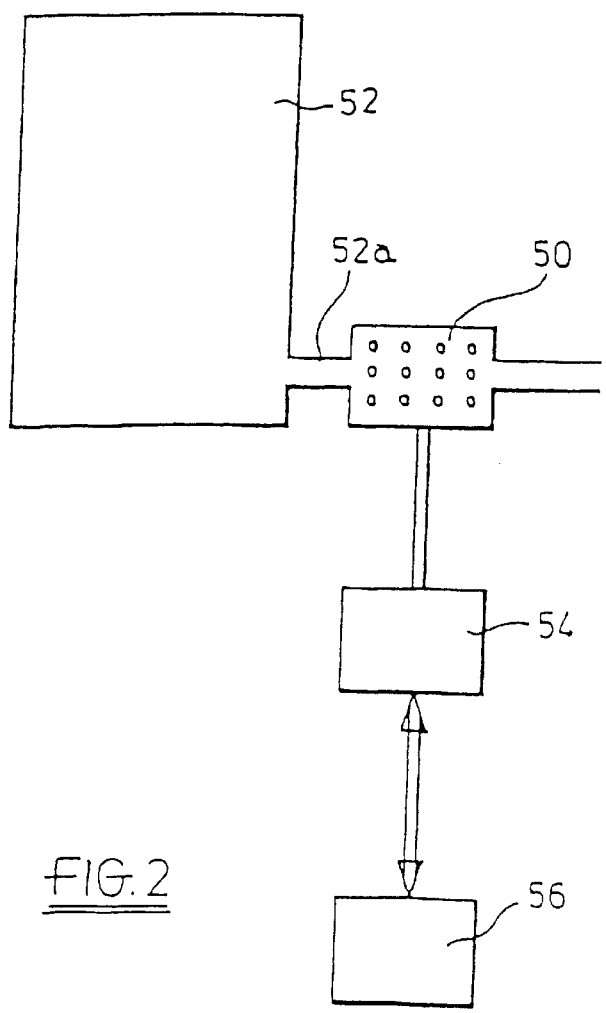
FIG. 2 shows a second detector according to the invention.

The emitted respiratory gases can be obtained from a ventilator. FIG. 2 depicts such an arrangement, in which emitted respiratory gases are exhausted from the output 52a of a ventilator 52. An array of gas sensors 50 is directly connected to the output 52a of the ventilator, and thus continuously samples the respiratory gases of the subject. As described above, a single gas sensor might be provided. The gas sensing device is defined by the gas sensors 50, measurement means 54 for measuring the response of the gas sensors 50, and a computer 56, employed to control the overall gas sensing procedure and for data analysis purposes. It may be necessary to include filters or concentrators into the system. It is possible to reduce water content or to concentrate low levels of important volatiles using Tenax tubes, affinity columns and other purge and trap systems.

EXAMPLE

Measurements were performed on the respiratory gases, obtained from ventilators, of two patients presenting with pulmonary candida albicans, using a thirty two sensor semiconducting polymer instrument (AromaScan A32S). Measurements of response patterns were made once a day over a period of five days.

Figure 3:
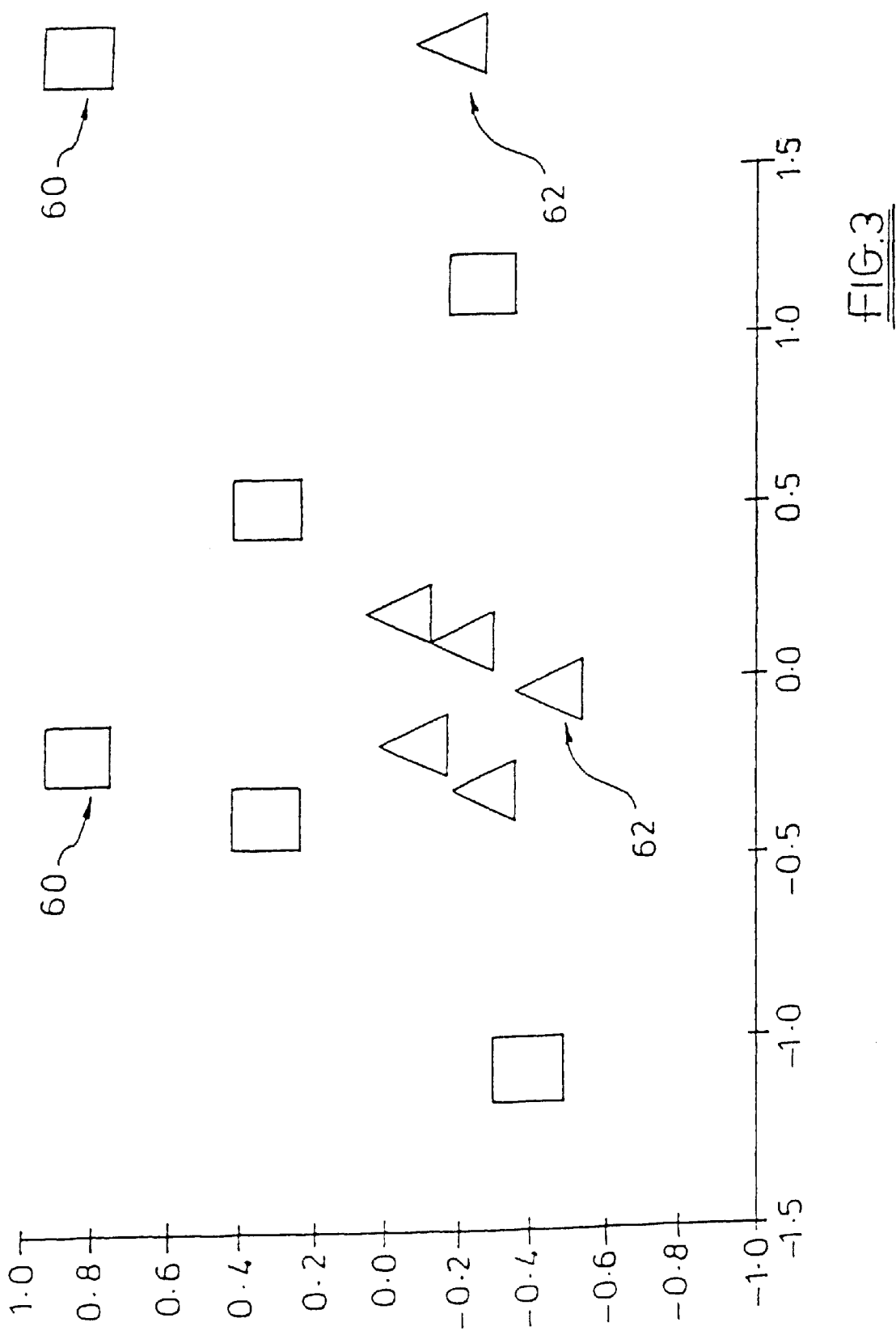
FIG. 3 shows response on a function of time for two patients presenting with pulmonary condition albicans.

FIG. 3 shows the results in the form of a Sammon map (in which response patterns are reduced to a two dimensional coordinate), the rectangles 60 representing measurements of the respiratory gases of a first patient, and the triangles 62 representing measurements of the respiratory gases of a second patient. The data obtained from the second patient are quite stable, the response patterns being grouped in a tight cluster. This correlates with the fact that the patient was very stable, subsequently making an excellent recovery. In contrast, the response patterns obtained from the first patient vary greatly from day to day. This correlates with the fact that the patient was very unstable, and died on the fifth day of measurements.

There are numerous conditions which may be detected using the method of the present invention. Examples include lung disorders, such as pneumonia, lung cancer, tuberculosis or yeast infections such as candida albicans, and gastrointestinal infections, such as those caused by helicobacter. Additionally, diabetes may be detected via a patient's breath, due to the presence of characteristic aldehydes and ketones, and the presence of alcohol in the patient's system can be detected by detecting same in the breath. Halitosis is also detectable, as is the occurrence of the liver disorder PKU (phenylketonumia). The latter is at present detected via urine tests. Other infections or disease conditions, such as heart disease, might be detectable. The technique may be used for screening purposes, for example in pre-clinical trials or in the detection of drugs.

When monitoring is performed on-line using a ventilator, it is possible to interface the system to a drug delivery system so that optimal quantities of antibiotics or other drugs are administered. It is possible to select which drugs are administered depending on the analysis performed on the respiratory gases. Alternatively, or additionally, data fusion is possible in which the data provided by the present invention is combined with data from other sources, such as temperature, blood pressure carbon dioxide levels, oxygen levels, data on anaesthetic gases and data on blood chemistry, to provide a vital signs index.

What is claimed is:

1. A diagnostic method for diagnosis the condition of a patient comprising:

introducing exhaled respiratory gas of a subject to a gas sensing device having an array of gas sensors, detecting certain species in he exhaled respiratory gas with said device and producing a output pattern according to said certain species, correlating the output pattern with a plurality of known output patterns, each of said known output patterns corresponding to a different condition of the patient, diagnosing a condition of the patient based on said correlation.

2. A method according to claim 1 in which the subject is a human.

3. A method according to claims 1 or 2 in which the gas sensing device comprises a gas sensitive material.

4. A method according to claim 3 in which an electrical property of the gas sensitive material varies on exposure to gases.

5. A method according to claim 4 in which the gas sensitive material comprises semiconducting organic polymer.

6. A method according to claim 1 in which the emitted respiratory gases are obtained from a ventilator.

7. A method according to claim 1 in which the emitted subject respiratory gases are introduced directly to said gas sensing device.

8. A method according to claim 1 in which the occurrence of an infection or a disease state is detected.

9. A method according to claim 1 in which the occurrence of a lung disorder is detected.

10. A method according to claim 9 in which the lung disorder is pneumonia, tuberculosis or a yeast infection.

11. A method according to claim 1 in which the occurrence of a gastrointestinal infection is detected.

12. A method according to claim 1 in which the occurrence of diabetes is detected.

13. A method according to claim 1 in which the presence of alcohol is detected.

14. A method according to claim 1 in which the occurrence of phenylketonuria is detected.

15. A detector for detecting the occurrence of a condition in a respiring subject comprising:

a gas sensing device including an array of gas sensors responsive to certain species and configured to generate response signals in response to said certain species, said gas sensing device structured to produce an output signal corresponding to said response signals;

means for introducing respiratory gases exhaled by a subject to said gas sensing device;

a correlator configured to correlate the output pattern with a plurality of known output patterns, each of said known output patterns corresponding to a different condition of a subject, a diagnoser configured to recognize the occurrence of a condition in the respiring subject from the output pattern correlation.

16. A detector according to claim 14 in which the means for introducing respiratory gases to the gas sensing device comprises a ventilator.

17. A detector according to claim 16 in which the gas sensing device is directly connected to the ventilator.

18. A detector according to claim 15 in which the gas sensing device comprises a gas sensitive material having an electrical property variable in relation to exposure of the gas sensitive material to a gas species, said gas sensitive material comprising semiconducting organic polymer.

19. A detector according to claim 15 in which the means adapted to recognize the occurrence of a condition comprises means adapted to recognize the occurrence of a lung disorder including at least one of pneumonia, tuberculosis and a yeast infection.

* * * * *

UNITED STATES PATENT AND TRADEMARK OFFICE
CERTIFICATE OF CORRECTION

PATENT NO. : 6,620,107 B2  
DATED : September 16, 2003  
INVENTOR(S) : Payne et al.

It is certified that error appears in the above-identified patent and that said Letters Patent is hereby corrected as shown below:

<u>Title page,</u>  
Item [30], Foreign Application Priority Data, "Mar. 6, 1997  (GB).......9704676" should read -- Mar. 6, 1997  (GB)........9704676.7 --.

<u>Column 1,</u>  
Line 16, "for detection numerous" should read -- for detecting numerous --.  
Line 24, "subject repiratory gases" should read -- subject respiratory gases --.  
Line 61, "is adapted to" should read -- is adapted to --.

<u>Column 4,</u>  
Line 27, "according to claims 1 or 2 in" should read -- according to claim 1 in --.

<u>Column 5,</u>  
Line 4, according to claim 14 in" should read -- according to claim 15 in --.

Signed and Sealed this

Thirteenth Day of July, 2004

JON W. DUDAS  
*Acting Director of the United States Patent and Trademark Office*